United States Patent
Hood et al.

(10) Patent No.: US 11,583,437 B2
(45) Date of Patent: Feb. 21, 2023

(54) REUSABLE WARMING BLANKET WITH PHASE CHANGE MATERIAL

(71) Applicant: Aspen Surgical Products, Inc., Caledonia, MI (US)

(72) Inventors: Michael S. Hood, Batesville, IN (US); Charles A. Lachenbruch, Batesville, IN (US); David L. Bedel, Oldenburg, IN (US); Robert J. Lawrence, Grand Rapids, MI (US); Darrell L. Borgman, Batesville, IN (US); Varad N. Srivastava, Skaneateles, NY (US); Neal Wiggermann, Batesville, IN (US); Kirsten M. Emmons, Batesville, IN (US); Frank E. Sauser, Cincinnati, OH (US); Holly L. Bengel, Lowell, MI (US); Logan Cobler, Osgood, IN (US); Kayla Stevens, Skaneateles, NY (US); Justine Pringle, Grand Rapids, MI (US); Ryan S. Severns, Grand Rapids, MI (US); Yongji Fu, Harrison, OH (US)

(73) Assignee: Aspen Surgical Products, Inc., Caledonia, MI (US)

( * ) Notice: Subject to any disclaimer, the term of this patent is extended or adjusted under 35 U.S.C. 154(b) by 1061 days.

(21) Appl. No.: 16/259,030

(22) Filed: Jan. 28, 2019

(65) Prior Publication Data

US 2019/0240066 A1 Aug. 8, 2019

Related U.S. Application Data

(60) Provisional application No. 62/718,507, filed on Aug. 14, 2018, provisional application No. 62/626,877, filed on Feb. 6, 2018.

(51) Int. Cl.
*A61F 7/00* (2006.01)
*B32B 7/12* (2006.01)
(Continued)

(52) U.S. Cl.
CPC .......... *A61F 7/0097* (2013.01); *A47G 9/0215* (2013.01); *A61F 7/02* (2013.01);
(Continued)

(58) Field of Classification Search
CPC ............ A47G 2200/16; A47G 2400/10; A47G 9/0215; A61B 90/92; A61B 90/94;
(Continued)

(56) References Cited

U.S. PATENT DOCUMENTS

| 4,391,267 A | 7/1983 | Arrhenius |
| 4,504,402 A | 3/1985 | Chen et al. |

(Continued)

FOREIGN PATENT DOCUMENTS

| EP | 2175398 A1 | 4/2010 |
| EP | 1635757 B1 | 6/2010 |

(Continued)

OTHER PUBLICATIONS

US 6,645,236 B2, 11/2003, Lachenbruch et al. (withdrawn)
(Continued)

*Primary Examiner* — Dana Ross
*Assistant Examiner* — James F Sims, III
(74) *Attorney, Agent, or Firm* — Price Heneveld LLP

(57) ABSTRACT

A warming device may include a batting layer having a phase change material. The batting layer may have a patient side and an upper side. A hot melt fabric adhesive may be applied to the patient side and upper side of the batting. A first fabric layer may be adhered to the hot melt fabric on the patient side of the batting. The first fabric layer may have a phase change material integrated coating. An insulation
(Continued)

layer may be adhered to the hot melt fabric on the upper side of the batting. A second fabric layer may be coupled to the insulation layer.

15 Claims, 6 Drawing Sheets

(51) Int. Cl.
| | | |
|---|---|---|
| B32B 5/26 | (2006.01) | |
| A61F 7/02 | (2006.01) | |
| B32B 5/02 | (2006.01) | |
| A47G 9/02 | (2006.01) | |
| H05B 3/34 | (2006.01) | |
| A61B 90/94 | (2016.01) | |
| A61B 90/92 | (2016.01) | |

(52) U.S. Cl.
CPC ............... *B32B 5/022* (2013.01); *B32B 5/26* (2013.01); *B32B 7/12* (2013.01); *H05B 3/347* (2013.01); *A47G 2200/16* (2013.01); *A47G 2400/10* (2013.01); *A61B 90/92* (2016.02); *A61B 90/94* (2016.02); *A61F 2007/0009* (2013.01); *A61F 2007/0036* (2013.01); *A61F 2007/0041* (2013.01); *A61F 2007/0045* (2013.01); *A61F 2007/0244* (2013.01); *A61F 2007/0292* (2013.01); *B32B 2262/0276* (2013.01); *B32B 2262/062* (2013.01); *B32B 2307/30* (2013.01)

(58) Field of Classification Search
CPC ...... A61F 2007/0009; A61F 2007/0036; A61F 2007/0041; A61F 2007/0045; A61F 2007/0244; A61F 2007/0292; A61F 7/0097; A61F 7/02; B32B 2262/0276; B32B 2262/062; B32B 2307/30; B32B 5/022; B32B 5/26; B32B 7/12; H05B 3/347
USPC .......................................................... 607/96
See application file for complete search history.

(56) References Cited

U.S. PATENT DOCUMENTS

| | | |
|---|---|---|
| 4,596,250 A | 6/1986 | Beisang et al. |
| 4,651,369 A | 3/1987 | Guldager |
| 4,667,658 A | 5/1987 | Guibert |
| 4,671,267 A | 6/1987 | Stout |
| 4,699,134 A | 10/1987 | Samuelsen |
| 4,708,812 A | 11/1987 | Hatfield |
| 4,756,299 A | 7/1988 | Podella |
| 4,807,696 A | 2/1989 | Colvin et al. |
| 4,911,232 A | 3/1990 | Colvin et al. |
| 4,914,717 A | 4/1990 | Gibbon |
| 4,962,761 A | 10/1990 | Golden |
| 4,964,402 A | 10/1990 | Grim et al. |
| 4,981,135 A | 1/1991 | Hardy |
| 4,999,867 A | 3/1991 | Toivio et al. |
| 5,010,608 A | 4/1991 | Barnett et al. |
| 5,033,136 A | 7/1991 | Elkins |
| 5,069,208 A | 12/1991 | Noppel et al. |
| 5,072,455 A | 12/1991 | Thomas |
| 5,088,487 A | 2/1992 | Turner |
| 5,094,238 A | 3/1992 | Gibbon |
| 5,181,905 A | 1/1993 | Flam |
| 5,190,031 A | 3/1993 | Guibert et al. |
| 5,211,949 A | 5/1993 | Salyer |
| 5,275,156 A | 1/1994 | Milligan et al. |
| 5,277,180 A | 1/1994 | Angelillo et al. |
| 5,300,103 A | 4/1994 | Stempel et al. |
| 5,366,801 A | 11/1994 | Bryant et al. |
| 5,431,622 A | 7/1995 | Pyrozyk et al. |
| 5,443,487 A | 8/1995 | Guibert et al. |
| 5,456,704 A | 10/1995 | Kilcullen |
| 5,456,852 A | 10/1995 | Isiguro |
| 5,486,207 A | 1/1996 | Mahawili |
| 5,511,260 A | 4/1996 | Dinsmoor, III et al. |
| 5,575,815 A | 11/1996 | Slepian et al. |
| 5,630,961 A | 5/1997 | Salee |
| 5,637,389 A | 6/1997 | Colvin et al. |
| 5,691,040 A | 11/1997 | Barbeau et al. |
| 5,702,375 A | 12/1997 | Angelillo et al. |
| 5,713,143 A | 2/1998 | Kendall |
| 5,722,482 A | 3/1998 | Buckley |
| 5,737,774 A | 4/1998 | , I et al. |
| 5,750,962 A | 5/1998 | Hyatt |
| 5,800,480 A | 9/1998 | Augustine et al. |
| 5,817,145 A | 10/1998 | Augustine et al. |
| 5,837,002 A | 11/1998 | Augustine et al. |
| 5,887,437 A | 3/1999 | Maxim |
| 5,926,884 A | 7/1999 | Biggie et al. |
| 5,932,129 A | 8/1999 | Hyatt |
| 5,964,723 A | 10/1999 | Augustine |
| 5,984,953 A | 11/1999 | Sabin et al. |
| 5,993,480 A | 11/1999 | Burrows |
| 6,004,662 A | 12/1999 | Buckley |
| 6,007,572 A | 12/1999 | Baldwin |
| 6,010,528 A | 1/2000 | Augustine et al. |
| 6,033,432 A | 3/2000 | Augustine et al. |
| 6,040,493 A | 3/2000 | Cooke et al. |
| 6,071,254 A | 6/2000 | Augustine |
| 6,071,304 A | 6/2000 | Augustine et al. |
| 6,080,189 A | 6/2000 | Augustine et al. |
| 6,083,254 A | 7/2000 | Evans |
| 6,083,256 A | 7/2000 | Der Ovanesian |
| 6,095,992 A | 8/2000 | Augustine |
| 6,102,936 A | 8/2000 | Augustine et al. |
| 6,113,561 A | 9/2000 | Augustine |
| 6,119,474 A | 9/2000 | Augustine et al. |
| 6,120,530 A | 9/2000 | Nuckols et al. |
| 6,123,716 A | 9/2000 | Augustine et al. |
| 6,132,455 A | 10/2000 | Shang |
| 6,179,879 B1 | 1/2001 | Robinson et al. |
| 6,183,855 B1 | 2/2001 | Buckley |
| 6,497,720 B1 | 12/2002 | Augustine et al. |
| 6,699,266 B2 | 3/2004 | Lachenbruch et al. |
| 6,755,852 B2 | 6/2004 | Lachenbruch et al. |
| 6,763,671 B1 | 7/2004 | Klett et al. |
| 6,772,825 B2 | 8/2004 | Lachenbruch et al. |
| 6,904,956 B2 | 6/2005 | Noel |
| 6,996,864 B2 | 2/2006 | Call |
| 7,043,768 B2 | 5/2006 | Gogarty |
| 7,048,976 B2 | 5/2006 | Caceres et al. |
| 7,191,478 B2 | 3/2007 | Schmidt |
| 7,238,196 B2 | 7/2007 | Wibaux |
| 7,240,720 B2 | 7/2007 | Noel |
| 7,273,490 B2 | 9/2007 | Lachenbruch |
| 7,452,339 B2 | 11/2008 | Mattison |
| 7,588,548 B2 | 9/2009 | Kopreski |
| 7,708,338 B2 | 5/2010 | Wolas |
| 7,727,267 B2 | 6/2010 | Lachenbruch |
| 7,766,950 B2 | 8/2010 | Castellani et al. |
| 7,780,713 B2 | 8/2010 | Roberts |
| 7,793,372 B2 | 9/2010 | Lean et al. |
| 7,854,754 B2 | 12/2010 | Ting et al. |
| 8,002,721 B2 | 8/2011 | Bretl et al. |
| 8,062,343 B2 | 11/2011 | Augustine et al. |
| 8,065,763 B2 | 11/2011 | Brykalski et al. |
| 8,100,848 B2 | 1/2012 | Wilkes et al. |
| 8,129,580 B2 | 3/2012 | Wilkes et al. |
| 8,133,211 B2 | 3/2012 | Cavanaugh, II et al. |
| 8,147,468 B2 | 4/2012 | Barta et al. |
| 8,167,856 B2 | 5/2012 | Kazala, Jr. et al. |
| 8,172,816 B2 | 5/2012 | Kazala, Jr. et al. |
| 8,181,290 B2 | 5/2012 | Brykalski et al. |
| 8,187,237 B2 | 5/2012 | Seegert |
| 8,188,331 B2 | 5/2012 | Barta et al. |
| 8,191,187 B2 | 6/2012 | Brykalski et al. |
| 8,192,474 B2 | 6/2012 | Levinson |
| 8,202,261 B2 | 6/2012 | Kazala, Jr. et al. |
| 8,241,261 B2 | 8/2012 | Randolph et al. |

(56) References Cited

U.S. PATENT DOCUMENTS

| | | |
|---|---|---|
| 8,275,442 B2 | 9/2012 | Allison |
| 8,277,497 B2 | 10/2012 | Noel |
| 8,285,390 B2 | 10/2012 | Levinson et al. |
| 8,292,936 B2 | 10/2012 | Jung |
| 8,292,937 B2 | 10/2012 | Von Hoffmann et al. |
| 8,303,857 B2 | 11/2012 | Seeboth et al. |
| 8,326,426 B2 | 12/2012 | Thornton et al. |
| 8,327,477 B2 | 12/2012 | Lachenbruch et al. |
| 8,332,975 B2 | 12/2012 | Brykalski et al. |
| 8,337,539 B2 | 12/2012 | Ting et al. |
| 8,376,232 B2 | 2/2013 | Eckstein et al. |
| 8,399,730 B2 | 3/2013 | Kazala, Jr. et al. |
| 8,402,579 B2 | 3/2013 | Marquette et al. |
| 8,418,286 B2 | 4/2013 | Brykalski et al. |
| 8,603,073 B2 | 5/2013 | Mlison |
| 8,523,927 B2 | 9/2013 | Levinson et al. |
| 8,528,833 B2 | 9/2013 | Munson |
| 8,578,527 B2 | 11/2013 | Lachenbruch et al. |
| 8,617,230 B2 | 12/2013 | Diller et al. |
| 8,621,687 B2 | 1/2014 | Brykalski et al. |
| 8,641,745 B2 | 2/2014 | Warner et al. |
| 8,673,448 B2 | 3/2014 | Hartmann et al. |
| 8,702,774 B2 | 4/2014 | Baker et al. |
| 8,722,959 B2 | 5/2014 | Wilkes et al. |
| 8,732,874 B2 | 5/2014 | Brykalski et al. |
| 8,782,830 B2 | 7/2014 | Brykalski et al. |
| 8,800,078 B2 | 8/2014 | Lachenbruch et al. |
| 8,856,993 B2 | 10/2014 | Richards et al. |
| 8,858,971 B2 | 10/2014 | Rao |
| 8,887,619 B2 | 11/2014 | Kallmyer et al. |
| 8,893,329 B2 | 11/2014 | Petrovski et al. |
| 8,933,140 B2 | 1/2015 | Peterson et al. |
| 8,937,212 B2 | 1/2015 | Fogg et al. |
| 9,009,892 B2 | 4/2015 | Lachenbruch et al. |
| 9,084,764 B2 | 7/2015 | Rao |
| 9,089,462 B1 | 7/2015 | Lafleche |
| 9,125,497 B2 | 9/2015 | Brykalski et al. |
| 9,132,031 B2 | 9/2015 | Levinson et al. |
| 9,158,141 B2 | 10/2015 | DeFranks |
| 9,234,059 B2 | 1/2016 | Hartmann et al. |
| 9,265,654 B2 | 2/2016 | Gallaher |
| 9,326,882 B2 | 5/2016 | Moulin |
| 9,333,136 B2 | 5/2016 | Gibson et al. |
| 9,339,412 B2 | 5/2016 | Diller et al. |
| 9,375,345 B2 | 6/2016 | Levinson et al. |
| 9,408,475 B2 | 8/2016 | Mikkelsen et al. |
| 2001/0039391 A1 | 11/2001 | Augustine |
| 2002/0086204 A1* | 7/2002 | Rock ............ H05B 3/347 219/209 |
| 2003/0046762 A1 | 3/2003 | Stolpmann |
| 2003/0109816 A1 | 6/2003 | Lachenbruch et al. |
| 2003/0109908 A1 | 6/2003 | Lachenbruch et al. |
| 2003/0109910 A1 | 6/2003 | Lachenbruch et al. |
| 2005/0049662 A1 | 3/2005 | Purcell |
| 2005/0076715 A1 | 4/2005 | Kuklis et al. |
| 2005/0145372 A1 | 7/2005 | Noel |
| 2006/0100682 A1 | 5/2006 | Koffroth |
| 2006/0184216 A1 | 8/2006 | Van Duren |
| 2006/0260058 A1 | 11/2006 | Schmidt |
| 2006/0276089 A1 | 12/2006 | Amarasinghe et al. |
| 2007/0098973 A1 | 5/2007 | Wagner et al. |
| 2007/0101478 A1 | 5/2007 | Koscheyev et al. |
| 2007/0135878 A1 | 6/2007 | Lachenbruch et al. |
| 2007/0173154 A1 | 7/2007 | Hartmann et al. |
| 2007/0193278 A1 | 8/2007 | Polacek et al. |
| 2007/0198071 A1 | 8/2007 | Ting et al. |
| 2007/0250025 A1 | 10/2007 | Sams et al. |
| 2007/0255362 A1 | 11/2007 | Levinson et al. |
| 2008/0015665 A1 | 1/2008 | Lachenbruch |
| 2008/0028517 A1 | 2/2008 | Schmidt |
| 2008/0077201 A1 | 3/2008 | Levinson et al. |
| 2008/0120761 A1 | 5/2008 | Yang et al. |
| 2008/0140166 A1 | 6/2008 | von Hoffman et al. |
| 2008/0234789 A1 | 9/2008 | Freeland et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0076574 A1 | 3/2009 | Noel |
| 2009/0076575 A1 | 3/2009 | Noel |
| 2009/0293887 A1 | 12/2009 | Wilkes et al. |
| 2009/0299249 A1 | 12/2009 | Wilkes et al. |
| 2009/0299256 A1 | 12/2009 | Barta et al. |
| 2009/0299307 A1 | 12/2009 | Barta et al. |
| 2009/0299308 A1 | 12/2009 | Kazala, Jr. et al. |
| 2009/0299442 A1 | 12/2009 | Vergona et al. |
| 2010/0011489 A1 | 1/2010 | Goldmann et al. |
| 2010/0012883 A1 | 1/2010 | Hartmann et al. |
| 2010/0015430 A1 | 1/2010 | Hartmann et al. |
| 2010/0016513 A1 | 1/2010 | Hartmann et al. |
| 2010/0089381 A1 | 4/2010 | Bolmer et al. |
| 2010/0227542 A1 | 9/2010 | Goldmann et al. |
| 2010/0263128 A1 | 10/2010 | Lean et al. |
| 2010/0274331 A1 | 10/2010 | Williamson et al. |
| 2010/0280582 A1 | 11/2010 | Baker et al. |
| 2011/0024076 A1 | 2/2011 | Lachenbruch et al. |
| 2011/0041780 A1 | 2/2011 | Hurwitz |
| 2011/0092890 A1 | 4/2011 | Stryker et al. |
| 2011/0127248 A1 | 6/2011 | Moreshead |
| 2011/0128686 A1 | 6/2011 | Moreshead |
| 2011/0128726 A1 | 6/2011 | Moreshead |
| 2011/0130813 A1 | 6/2011 | Moreshead |
| 2011/0183712 A1 | 7/2011 | Eckstein et al. |
| 2012/0023664 A1 | 2/2012 | Joo et al. |
| 2012/0095538 A1 | 4/2012 | Dow |
| 2012/0180225 A1 | 7/2012 | Gladney et al. |
| 2012/0330213 A1 | 12/2012 | Valdez |
| 2013/0043232 A1 | 2/2013 | Whitworth et al. |
| 2013/0205462 A1 | 8/2013 | Kitaura et al. |
| 2013/0296769 A1 | 11/2013 | Howell et al. |
| 2014/0141233 A1 | 5/2014 | Crawford et al. |
| 2014/0221962 A1 | 8/2014 | Ribble et al. |
| 2014/0266643 A1 | 9/2014 | Receveur et al. |
| 2014/0304915 A1 | 10/2014 | Lachenbruch |
| 2014/0359939 A1 | 12/2014 | Carlitz |
| 2015/0013073 A1 | 1/2015 | Schwirian et al. |
| 2016/0235210 A1 | 8/2016 | Lachenbruch et al. |

FOREIGN PATENT DOCUMENTS

| | | |
|---|---|---|
| EP | 2272473 A2 | 1/2011 |
| EP | 1895874 B1 | 5/2012 |
| EP | 2276437 B1 | 12/2012 |
| EP | 2594234 A2 | 5/2013 |
| EP | 2344988 B1 | 8/2013 |
| EP | 2702966 A2 | 3/2014 |
| FR | 2643814 A1 | 9/1990 |
| FR | 2867672 A1 | 9/2005 |
| GB | 2510154 A | 7/2014 |
| GB | 2514594 A | 12/2014 |
| WO | 0212607 A2 | 2/2002 |
| WO | 2005006896 A1 | 1/2005 |
| WO | 2005016074 A1 | 2/2005 |
| WO | 2005067837 A1 | 7/2005 |
| WO | 2006001980 A2 | 1/2006 |
| WO | 2006122555 A1 | 11/2006 |
| WO | 2006122556 A1 | 11/2006 |
| WO | 2007133839 A1 | 11/2007 |
| WO | 2009046155 A1 | 4/2009 |
| WO | 2010075293 A1 | 7/2010 |
| WO | 2012174276 A2 | 12/2012 |
| WO | 2013177148 A1 | 11/2013 |
| WO | 2014008182 A1 | 1/2014 |
| WO | 2014035792 A1 | 3/2014 |
| WO | 2014182767 A1 | 11/2014 |
| WO | 2015006407 A1 | 1/2015 |

(56) References Cited

FOREIGN PATENT DOCUMENTS

| | | |
|---|---|---|
| WO | 2015137999 A1 | 9/2015 |
| WO | 2015188956 A1 | 12/2015 |

OTHER PUBLICATIONS

US 8,435,230 B2, 05/2013, Mlison (withdrawn)
US 9,398,814 B2, 07/2016, Richards et al. (withdrawn)
Extended European Search Report for Application No. 19155109.2, dated Jun. 4, 2019, 7 pages.

* cited by examiner

FRONT   BACK

REUSABLE WARMING BLANKET WITH PHASE CHANGE MATERIAL

CROSS-REFERENCE TO RELATED APPLICATIONS

The present disclosure is a non-provisional patent application of, and claims priority to, U.S. Patent Application Ser. No. 62/626,877, filed Feb. 6, 2018 and titled "REUSABLE WARMING BLANKET WITH PHASE CHANGE MATERIAL" and U.S. Patent Application Ser. No. 62/718,507, filed Aug. 14, 2018 and titled "REUSABLE WARMING BLANKET WITH PHASE CHANGE MATERIAL," both of which are herein incorporated in their entirety.

BACKGROUND

The present disclosure relates to blankets for a patient in a healthcare facility and particularly, to warming blankets.

Pre-operative patients are generally nervous, agitated, or otherwise stressed. Providing comfort warming can improve patient satisfaction. Almost all hospitals use conventional cotton warming blankets preheated in warming cabinets to provide comfort to pre-operative patients. However, such blankets lose their heat within a couple of minutes. Caregivers and operating room managers have confirmed there is an unmet need in providing comfort warming to pre-operative patients.

Some hospitals may use disposable air-activated self-heating blankets to provide comfort warming for an extended period; the heat is typically generated by an exothermic reaction of iron powder oxidizing into rust—iron oxide ($Fe_2O_3$), although other elements have been used. However, the use of air-activated blankets is primarily limited to military, athletics, or emergency medical services. Moreover, air-activated blankets do not feel as comfortable as cotton, as they are typically made with synthetic nonwoven materials. There is also concern over the environmental impact from the disposal of large single-use air-activated blankets. Also air-activated blankets are generally expensive (typically over $15 per use).

SUMMARY

The present disclosure includes one or more of the features recited in the appended claims and/or the following features which, alone or in any combination, may comprise patentable subject matter.

In one aspect of the disclosed embodiments, a warming device may include a first fabric layer having a weldable fabric. A second fabric layer may have a weldable fabric. The second fabric layer may be coupled to the first fabric layer so that the weldable fabric of the second fabric layer faces the weldable fabric of the first fabric layer to form a pocket. A phase change material may be enclosed in the pocket.

In some embodiments, the weldable fabric on the first fabric layer may be a thermoplastic urethane. The weldable fabric on the second fabric layer may be a thermoplastic urethane. The first fabric layer may be at least one of cotton or a cotton-polyester blend. The second fabric layer may be at least one of cotton or a cotton-polyester blend. It may be any fabric that is comfortable for direct contact with human skin, such as those commonly used in clothing. The fabric layers, the weldable fabrics, and the phase change material may be configured to withstand temperatures of at least 71 degrees Celsius.

It may be desired that the phase change material is at least one of a powder or a granulated material. The phase change material may be carbon paraffin. The phase change material may have a melting point between approximately 37° C. and 44° C. The phase change material may be mixed with a carrier. The carrier may be at least one of oil, gel, rubber, or other pliable material. The phase change material may be mixed with a conductive material. The conductive material may be at least one of carbon fibers, graphene, carbon nanotubules, conductive polymers, or the oil-based carrier medium.

Alternatively, or in addition to, the pocket may be formed by bonding the weldable fabrics. The pocket may be formed by radiofrequency welding of the weldable fabrics. The pocket may include a plurality of channels, the phase change material being enclosed in each of the plurality of channels.

It may be contemplated that the weldable fabric of the first fabric layer is laminated to an inner side of the first fabric layer. The weldable fabric of the second fabric layer may be laminated to an inner side of the second fabric layer. The weldable fabric of the first fabric layer may be interwoven with the first fabric layer. The weldable fabric of the second fabric layer may be interwoven with the second fabric layer.

It is possible that an insulative material is coupled to an outer side of the first fabric layer, or in between the person-facing fabric and the laminate. A heating element may be provided to melt the phase change material.

In some embodiments, the warming device is a blanket. The warming device may be a pad or a plurality of pads. At least one electrical cable may electrically couple the plurality of pads.

In another aspect of the disclosed embodiments, a warming blanket may include a pair of fabric layers coupled together to form a plurality of channels. A plastic coating may line each of the plurality of channels. A phase change material may be enclosed within each of the plurality of channels. The pair of fabric layers, the plastic coating, and the phase change material may be configured to withstand temperatures of 71 degrees Celsius.

In some embodiments, the plastic coating is a thermoplastic urethane. The pair of fabric layers may be at least one of cotton or a cotton-polyester blend. The phase change material may be at least one of a powder or a granulated material. It may be mixed with rubber or gel to form a soft, pliable homogenous material.

It may be desired that the pocket or plurality of channels are formed by bonding the plastic coating. The plurality of channels may be formed by radio-frequency or ultrasonic welding of the plastic coating.

It may be contemplated that the plastic coating is laminated to an inner side of each of the pair of fabric layers. The plastic coating may be interwoven with each of the pair of fabric layers.

In yet another aspect of the disclosed embodiments, a warming device may include an outer shell defining a pocket. An insulating material may be positioned on an outer surface of the outer shell. A phase change material may be positioned within the pocket. A carrier may be mixed with the phase change material. A conductive material may be mixed with the phase change material.

It may be contemplated that the outer shell is at least one of cotton or a cotton-polyester blend. The warming device may be a blanket. The warming device may be a pad or a plurality of pads. At least one electrical cable may electrically couple the plurality of pads.

In some embodiments, the phase change material may be at least one of a powder or a granulated material. The phase change material may be carbon paraffin. The phase change material may have a melting point between approximately 37° C. and 44° C. A heating element may be provided to melt the phase change material.

It may be desired that the carrier is at least one of an oil or gel. The conductive material may at least one of carbon fibers, graphene, carbon nanotubules, or conductive polymers.

In another aspect of the disclosed embodiments, a method of manufacturing a warming device includes forming a first weldable fabric on a first fabric layer, and forming a second weldable fabric on a second fabric layer. The first fabric layer may be positioned on the second fabric so that the first weldable fabric is positioned adjacent the second weldable fabric. The first weldable fabric may be welded to the second weldable fabric to form at least one channel having an open end. The at least one channel may be filled with a phase change material. The open end of the at least one channel may be welded.

In some embodiments, the steps of welding further may include radio-frequency welding or ultrasonic welding.

It may be desired that the method include forming a plurality of channels. Forming a plurality of channels may include forming a first plurality of channels having open ends on a first side of the warming device, and forming a second plurality of channels having open end on a second side of the warming device. The method may also include filling the first plurality of channels from the first side of the warming device, and welding the open ends on the first side of the warming device. The method may also include filling the second plurality of channels from the second side of the warming device, and welding the open ends on the second side of the warming device.

In yet a further aspect of the disclosed embodiments, a warming device includes a batting layer that may have a phase change material. The batting may have a patient side and an upper side. A hot melt fabric adhesive may be applied to the patient side and upper side of the batting. A first fabric layer may be adhered to the hot melt fabric on the patient side of the batting. The first fabric layer may have a phase change material integrated coating. An insulation layer may be adhered to the hot melt fabric on the upper side of the batting. A second fabric layer may be coupled to the insulation layer.

In some embodiments, the batting layer may include loosely-packed quilt batting.

Optionally, the first fabric layer may include microencapsulated phase change materials mixed into a fabric coating. The microencapsulated phase change materials may include a polymer shell coating around that maintains a solid appearance through phase changes between solid and liquid states. The microencapsulated phase change materials may have a temperature between 38 degrees Celsius and 44 degrees Celsius. The microencapsulated phase change materials may have a latent heat of over 200 KJ/kg.

It may be desired that a sealant be positioned between the patient side of the batting and the hot melt fabric, and a sealant be positioned between the upper side of the batting and the hot melt fabric. A sealant may be positioned between the first fabric layer and the hot melt fabric on the patient side of the batting.

It may be contemplated that the hot melt fabric is non-woven. The hot melt fabric may be formed from a powder.

Alternatively or in addition to, the first fabric layer may be formed from cotton. The first fabric layer may be formed from a poly fabric. The second fabric layer may be formed from cotton. The second fabric layer may be formed from a poly fabric.

Optionally, the insulation layer may be formed from polyester fiber.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Although this disclosure refers to specific embodiments, it will be understood by those skilled in the art that various changes in form and detail may be made without departing from the subject matter set forth in the accompanying claims.

Figure 1:
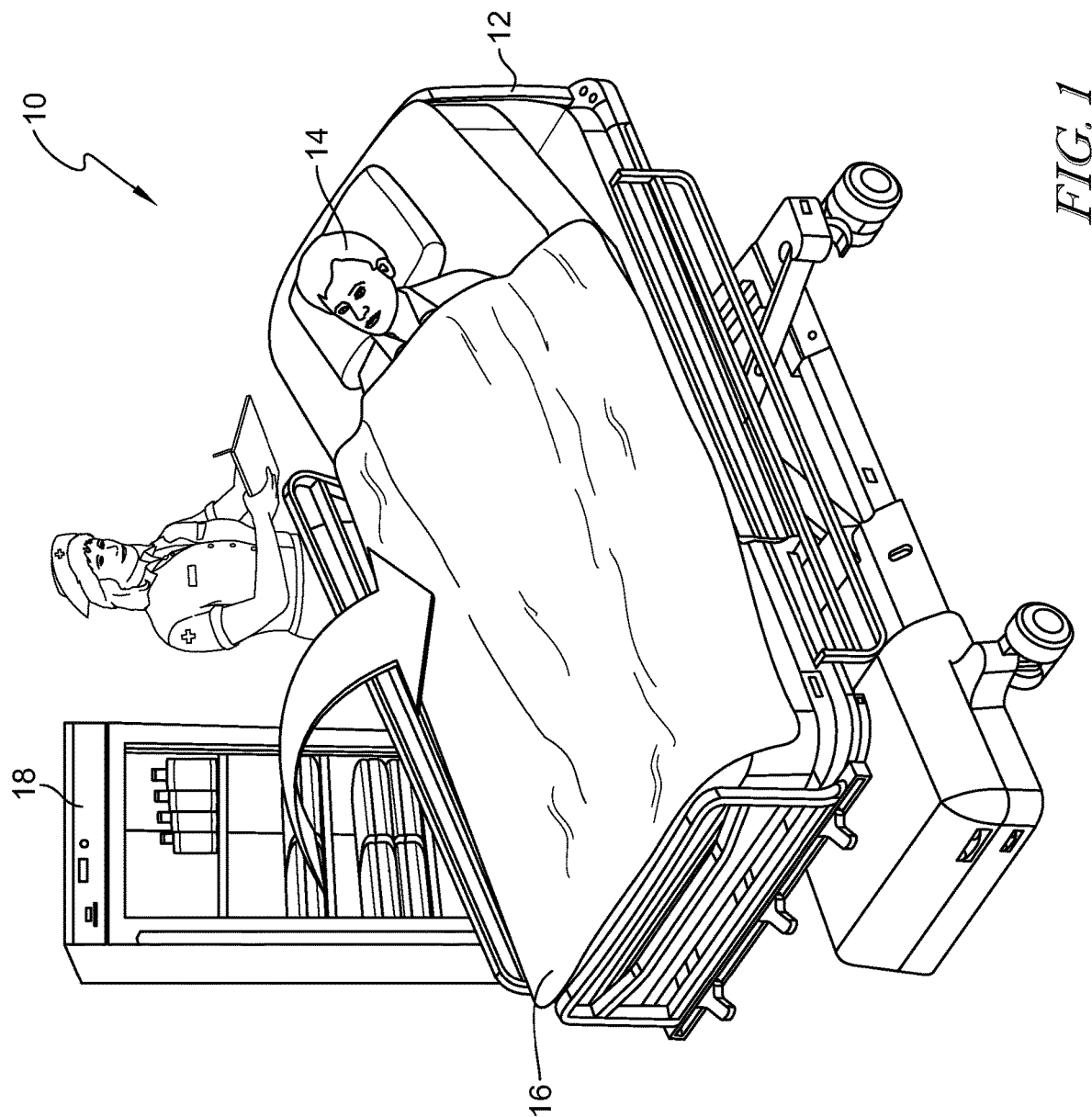
FIG. 1 is a perspective view of a patient room having a warming cabinet to warm a warming device for a patient positioned of a patient support apparatus.

Referring to FIG. 1, a patient room 10 includes a patient support apparatus 12. The patient support apparatus 12 is illustrated as a hospital bed; however, the patient support apparatus 12 may be a chair, a wheelchair, a stretcher, or any other apparatus for supporting a patient 14. The patient 14 is positioned on the patient support apparatus 12 and covered with a warming device 16. In the illustrated embodiment, the device 16 is a blanket. In other embodiments, the device 16 may be a pad or patch that is positioned on a part of the patient's body where the patient's blood flow is proximate to the patient's skin and a thickness of the patient's fat is limited. The areas of the patient's skin that are covered by the pad are selected based on areas that may require additional heating. The device 16 is configured to provide comfort-warming to the patient 14, e.g. prior to a surgical procedure. The device 16 may be used in a pre-operative room, a post-operative room, an intensive care unit, a Med-Surg unit, a long-term acute care facility, a long-term care facility or the like. The device 16 is configured to be warmed in a warming cabinet 18 that is illustrated in the patient room 10, but could be located in other areas of a healthcare facility.

The device 16 may be used by patients that are at risk of hypothermia, wherein a core temperature of the patient 14 is below 36° C. The patient 14 may be at risk for hypothermia because the patient's metabolic rate is reduced, the patient room 10 is cold, and/or the patient's protective vasoconstriction response is reduced. The device 16 also facilitates preventing milder reductions in core temperature, which may prolong recovery, prolong the patient's length of stay, increase a rate of infection, and/or increase cardiovascular issues. The device 16 is configured to maintain normothermia above 36° C. throughout a surgery and pre/post operation.

As discussed in more detail below, the device 16 is configured to retain its temperature for a greater period of time than a conventional warming blanket. For example, a conventional blanket that has been heated in a warming cabinet will typically retain its temperature for approximately one to two minutes. Because of the structure of the device 16, as described below, the device 16 may retain its temperature for at least fifteen minutes or longer.

Figure 2:
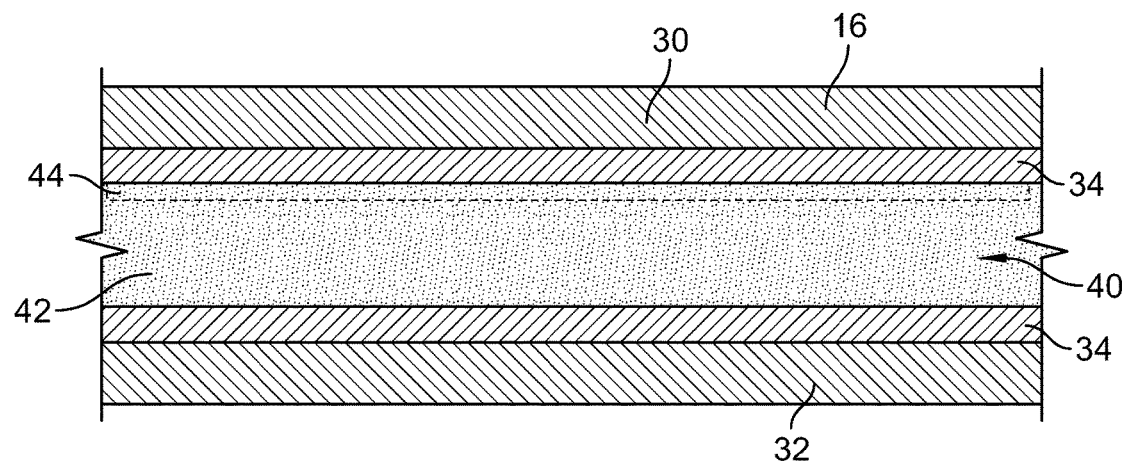
FIG. 2 is a cross-sectional view of the warming device shown FIG. 1.

As illustrated in FIG. 2, the device 16 includes fabric layers 30, 32. The fabric layers 30, 32 may be cotton fabric, cotton-polyester blend or the like and weigh approximately one pound. The fabric layers 30, 32 have an approximate width of 23-36 inches and an approximate length of 60 to 90 inches. The fabric layers 30, 32 may be colored and/or include a marking to distinguish the device 16 from conventional blankets in the healthcare facility. Each of the fabric layers 30, 32 is coated with a bonding material, e.g. thermoplastic film 34. In some embodiments, the thermoplastic film is laminated onto an inner side of each fabric layer 30, 32. In some embodiments, thermoplastic polymer particles are integrated into the fabric yarns 30, 32. The thermoplastic film 34 forms a flexible, impermeable, weldable fabric on the fabric layers 30, 32. The thermoplastic film 34 may be formed from polypropylene, nylon, or thermoplastic urethane. The thermoplastic urethane can sustain healthcare laundry cycle temperatures as high as 71° Celsius (160° Fahrenheit) for at least 25 minutes. The thermoplastic films 34 are ultrasonic- or radio-frequency weldable, thereby allowing the two thermoplastic films 34 to be bonded together with the same strength as the molecular structure the thermoplastic films 34. The thermoplastic films 34 are bonded together to join the fabric layers 30, 32 and form a pocket 40 for retaining a phase change material 42.

In some embodiments, the phase change material 42 may be carbon paraffin. The phase change material 42 has a melting point between 38° C. and 44° C. to allow the phase change material 42 to stay at that temperature when the device 16 is removed from the blanket warming cabinet and exposed to the human body which has an average skin temperature of 33 C 18. For example, 20-carbon paraffin has a melting point of approximately 36.7° C. 21-carbon paraffin has a melting point of approximately 40.2° C., and 22-carbon paraffin has a melting point of approximately 44° C. The phase change material 42 is configured to be charged in the warming cabinet 18 so that the phase change material 42 melts, i.e. changes phase. Generally, upon removing the device 16 from the blanket warming cabinet 18, the phase change material 42 needs to be higher than an average skin temperature of 33° C. in order to feel warm to the patient 14. A temperature of the device 16 in contact with the patient's skin cannot exceed 41° C. for over 15) minutes. By having a lower melting point than the temperature of the warming cabinet 18, the temperature of the phase change material change can drop when the device 16 is removed from the warming cabinet 18, which typically has a temperature of 54° C. This minimizes a risk of burning the patient and exceeding regulatory guidelines for heating human skin. In some embodiments, phase change materials with different melting points may be used to deliver different temperature levels to meet patient demand. For example, the three different phase change materials 42 may be heated to a warm temperature of 35° C., a warmer temperature of 38° C., or a hot temperature of 41° C., thereby providing a warm blanket, a warmer blanket, and a hot blanket. The phase change material 42 is selected to have a high latent heat, e.g. over 200 KJ/kg. The high latent heat enables the phase change material 42 to release heat at the melting temperature over a longer period of time. Additionally, the high latent heat enables the use of a smaller amount of phase change material 42, which minimizes a thickness, weight, and cost of the device 16. In some embodiments, the device 16 includes a charging element 44 (shown optionally in broken line). The charging element 44 may be powered to maintain the phase of the phase change material 42. A sensor and controller may be included to ensure the heater does not raise the PCM temperature above a specified level that would cause burning or exceeding regulatory limits. The charging element 44 may be electrically coupled to a power source.

The phase change material 42 may be enclosed in the device 16 in a non-toxic, non-flammable granular form or a powder form. Small particles allow the blanket 16 to retain shape and feel softer and more pliable to the patient 14 when the device 16 reaches room temperature and solid phase. The small particles also increase surface area and improve the conduction of heat to ensure consistent temperature profiles. Small particles are more easily mixable with carrier oils, intermixed with conductive materials, and integrated into gels, rubbers, etc. In some embodiments, the phase change material 42 may be a microencapsulated phase change material. In some embodiments, the phase change material 42 is an eutectic organic phase change material.

Figure 3:
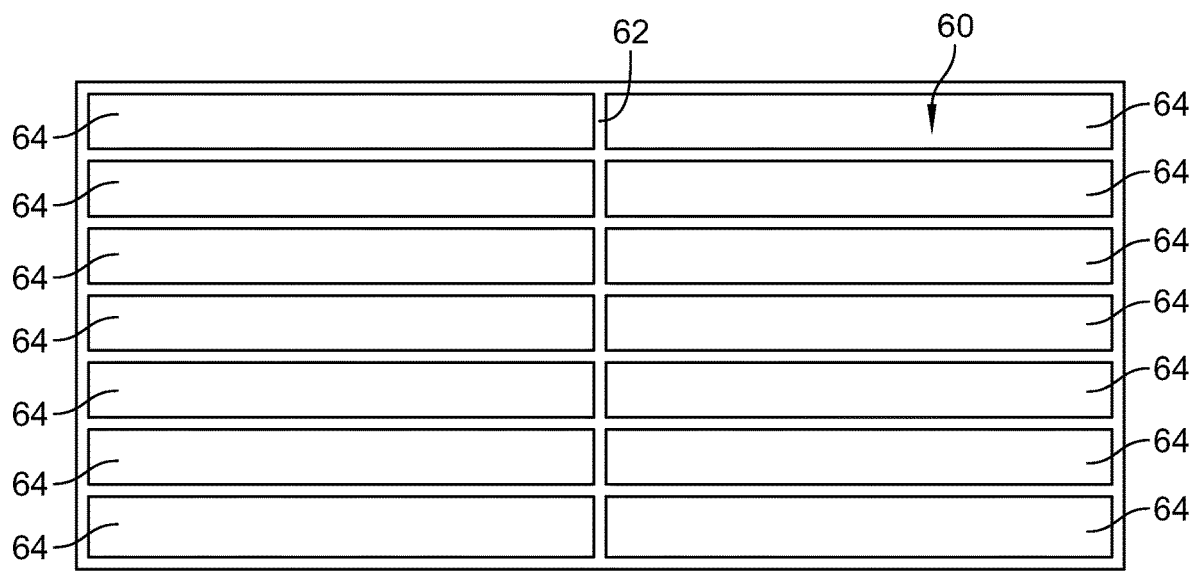
FIG. 3 is a top plan view of the device shown in FIG. 1 and illustrating the seams of the device.

Referring to FIG. 3, the fabric layers 30, 32 are sealed together to form a pocket 60. The fabric layers 30, 32 are positioned over one another with the thermoplastic films 34 facing one another. The thermoplastic films 34 are bonded together to join the fabric layers 30, 32. The thermoplastic films 34 are bonded together using radio-frequency or ultrasonic welding, which molecularly bonds the thermoplastic films 34 together along a seam 62. They may also be bonded using adhesives or other bonding methods. In some embodiments, a seam 62 is bonded around a perimeter of the fabric layers 30, 32 to form a single pocket 60 for receiving the phase change material 42. In the illustrative embodiment, multiple seams 62 are bonded to form a plurality of channels 64 within the pocket 60. As illustrated, the channels 64 are formed in columns and rows and have an open end 66. Any number of columns and rows of channels 64 may be formed. Alternatively, or in addition to, the channels 64 may take other configurations than columns and rows. Multiple channels 64 are created within the pocket 60 to hold the granules of phase change material 42 in place. The channels 64 prevent the phase change material 42 from shifting into thick and thin areas, thereby reducing comfort and patient satisfaction.

Figure 4:
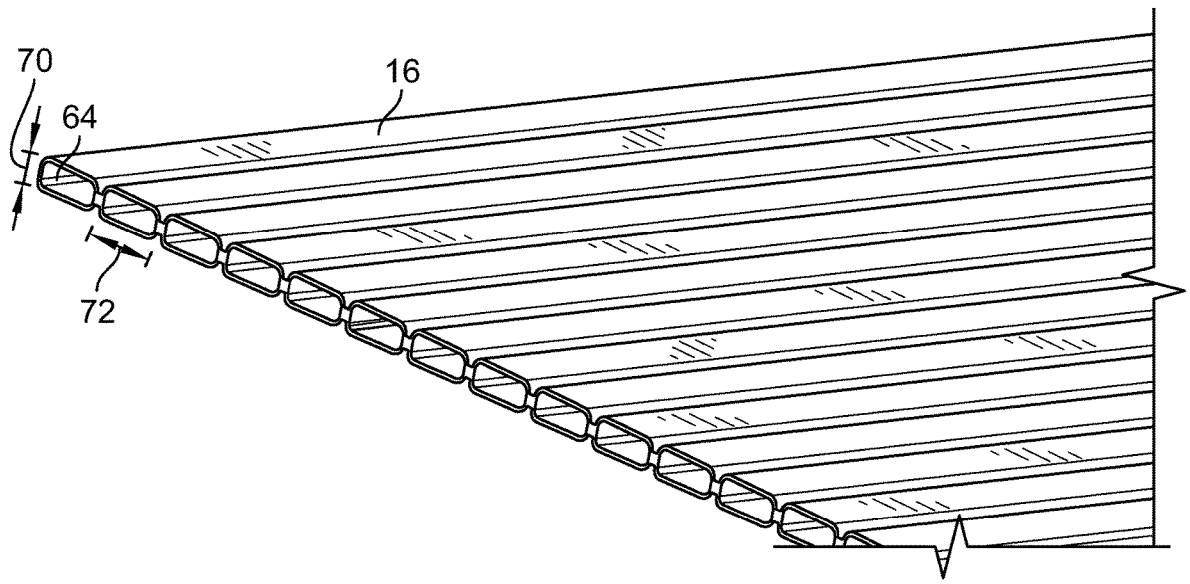
FIG. 4 is a cross-sectional view of the device taken along the line 4-4 shown in FIG. 3 and illustrating the channels of the device.

FIG. 4 illustrates a cross-sectional view of some of the channels 64. The channels 64 between ¼" and 2" wide in the direction 70, and between ⅛" and ⅜" thick in the direction 72. The channels 64 are illustrated as rectangles but may be any shape or form, e.g. circular. The plurality of channels 64 maintain a consistent thickness of the phase change material 42 throughout the device 16 to facilitate providing consistent temperatures across the device 16. Additionally, the channels 64 aid in manufacturing the device 16 by using gravity to allow the granular phase change material 42 to fill each channel 64. Multiple filling inflows may be used to fill all of the channels 64 simultaneously, thus reducing manufacturing time and cost. After the channels 64 are filled with phase change material 42 the open end 66 of each channel 64 is welded closed.

Figure 5:
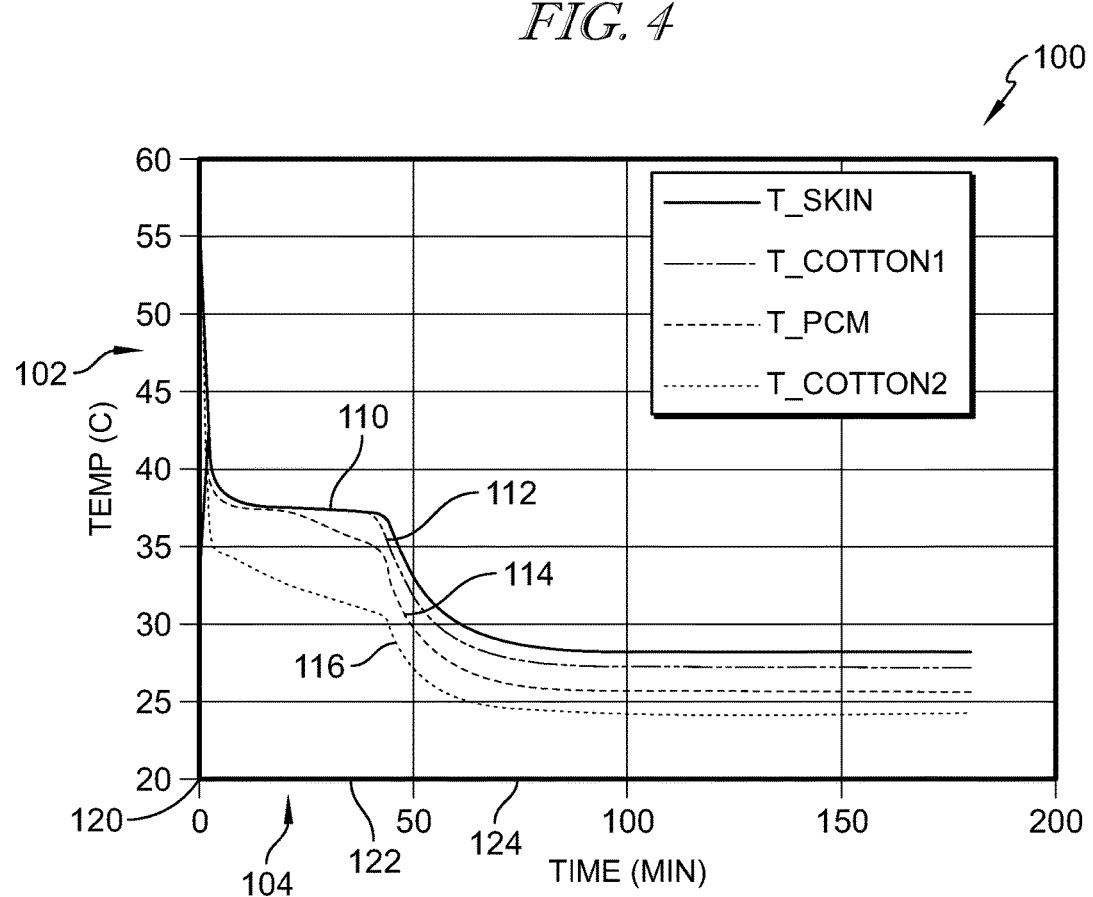
FIG. 5 is a graph illustrating heat retention in the device shown in FIG. 1 and a patient's skin.

Referring to FIG. 5, a graph 100 illustrates a temperature of several materials (y-axis 102) over time (x-axis 104) in a computer model. The temperature 102 is measured in degrees Celsius, and the time 104 is measured in minutes. Graph 100 includes a line 110 illustrating a temperature of the patient's skin over time. Upon positioning the device 16 on the patient 14 at minute zero 120, the temperature of the patient's skin is approximately 33° C. The temperature of the patient's skin then increases to approximately 38° C. Over the next 45 minutes from minute zero 120 to point 122; the patient's skin gradually decreases in temperature from 38° C. to 37° C. Accordingly, the temperature of the patient's skin is retained for approximately 45 minutes. After 45 minutes the temperature of the patient's skin may gradually decrease to approximately 28° C. at point 124.

Line 112 illustrates a temperature of fabric layer 30 over time, wherein fabric layer 30 is positioned against the patient's skin. Upon positioning the device 16 on the patient 14 at minute zero 120, the temperature of fabric layer 30 is approximately 54° C. 54° C. is approximately the temperature of the fabric layer 30 when the device 16 is removed from the warming cabinet 18. The temperature will rapidly drop as the blanket is exposed to room temperature of around 20 to 25 C. The temperature of fabric layer 30 then decreases to approximately 37° C., which is the melting point of the PCM in the computer model. Over the next 45 minutes from minute zero 120 to point 122, fabric layer 30 maintains a temperature of approximately 37° C. Accordingly, the temperature of fabric layer 30 is retained for approximately 45 minutes. After 45 minutes the temperature of fabric layer 30 gradually decreases to approximately 27° C. at point 124.

Line 114 illustrates a temperature of the phase change material 42 over time. Upon positioning the device 16 on the patient 14 at minute zero 120, the temperature of phase change material 42 may be approximately 54° C. 54° C. is approximately the temperature of the phase change material 42 when the device 16 is removed from the warming cabinet 18. The temperature of phase change material 42 then decreases to approximately 37° C. Over the next 45 minutes from minute zero 120 to point 122; phase change material 42 gradually decreases in temperature to a temperature of approximately 35° C. Accordingly, the temperature of phase change material 42 is relatively retained for approximately 45 minutes. After 45 minutes the temperature of phase change material 42 gradually decreases to approximately 26° C. at point 124.

Line 116 illustrates a temperature of fabric layer 32 over time, wherein fabric layer 32 is positioned away from the patient's skin. Upon positioning the device 16 on the patient 14 at minute zero 120, the temperature of fabric layer 32 is approximately 54° C. 54° C. is approximately the temperature of the fabric layer 32 when the device 16 is removed from the warming cabinet 18. The temperature of fabric layer 32 then decreases to approximately 34° C. Over the next 45 minutes from minute zero 120 to point 122; fabric layer 32 gradually decreases in temperature to a temperature of approximately 31° C. Accordingly, the temperature of fabric layer 32 is relatively retained for approximately 45 minutes. After 45 minutes the temperature of fabric layer 32 gradually decreases to approximately 25° C. at point 124.

As illustrated in the graph 100, the device 16 retains its temperature for approximately 45 minutes, which is a greater length of time than the one to two minutes that a convention blanket will retain its temperature. Because the device 16 retains its temperature a temperature of the patient's skin is retained at approximately 38° C. for approximately 45 minutes. It should be noted that graph 100 illustrates the temperature of a device 16 that has been heated to approximately 54° C. In other embodiments, the device 16 may be heated to temperatures greater or less than 54° C. In any embodiment, regardless of the temperature of the device 16, the blanket is configured to retain its temperature for a period of time that is greater than the time that a conventional blanket will retain its temperature.

The device 16 is configured to maintain heat longer than a conventional cotton warming blanket, which may lose heat in one to two minutes. Caregivers and other staff can use the device 16 without making changes to their work processes. During preparation, the device 16 may be pre-heated in the warming cabinet 18 along with traditional cotton warming blankets. In some embodiments, the device 16 may be stored in an optional insulated container (not shown) after being removed from the warming cabinet and before use to minimize heat loss while waiting to use the device 16 on the patient 14. This insulated container may be stored at the bedside to maximize the convenience for the caregiver.

The device 16 maintains a cotton feel unlike other blankets that use synthetic materials such as non-wovens and plastics. Additionally, the heavier weight provides comfort for the patient 14. The temperature of the device 16 stays within a comfortable range without overheating or burning the patient 14. The device 16 also allows a similar workflow for both caregivers and housekeeping staff, and only one blanket needed at a time, resulting in fewer trips to the warming cabinet to replace cooled blankets. The device 16 is also reusable and can be laundered at up to at least 160° F.

Figure 6:
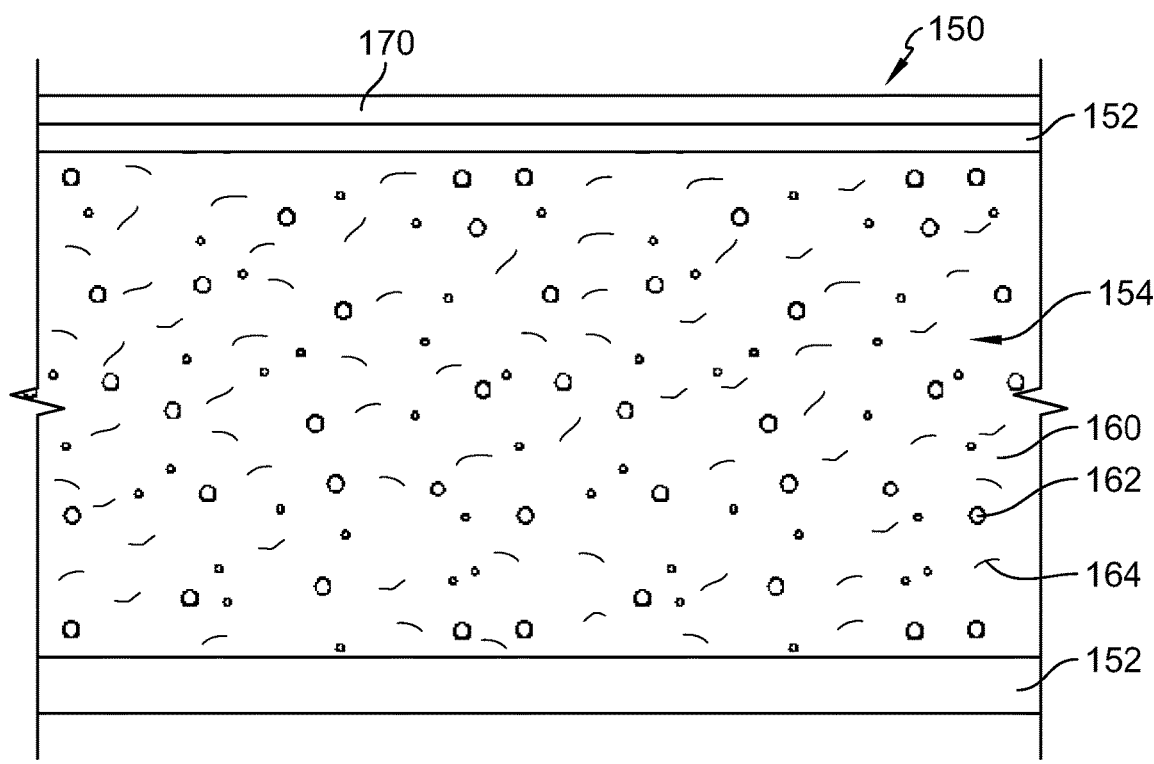
FIG. 6 is a cross-sectional view of another warming device formed in accordance with an embodiment.

FIG. 6 illustrates another warming device 150 formed in accordance with an embodiment and having an outer shell 152 that defines a pocket 154. The outer shell 152 may be formed from cotton fabric, cotton-polyester blend, plastic, or the like. In some embodiments, the outer shell 152 is formed from cotton fabric or cotton-polyester blend and includes a plastic inner liner within the pocket 154. The device 150 may include a single pocket 154 or a plurality of pockets 154 as described above. The pocket 154 is filled with a phase change material 160. The phase change material 160 may be carbon paraffin as discussed above.

The phase change material 160 is mixed with a pliable carrier 162, e.g. oil or a gel. Because the carrier 162 may have a low thermal conductivity, a conductive material 164 is also mixed with the phase change material 160 to enhance heat distribution. The conductive material 164 may include carbon fibers, graphene, carbon nanotubules, and/or conductive polymers; oil as a carrier may be sufficient as a thermally conductive material. The conductive material 164 may be powdered or chopped so that the conductive material 164 is conformable to the patient's body. Maintaining normothermia in a typically male generally requires approximately 120 Watts. With a typical heat fusion of 2.1 kJ/kg approximately seven pounds of phase change material 160 is required to maintain 120 Watts for four hours. Accordingly, in a 50% mixture of carrier 162 and phase change material 160, the device 150 weighs approximately 15 pounds. The device 150 may be altered based on the patient, e.g. male/female, patient weight, patient age. Additionally, the device 150 may be altered based on the length of the procedure being performed. As such, the weight and mixture concentrations of the device 150 may be altered.

An insulating material 170 is positioned on the outer shell 152. The insulating material 170 is positioned on one side of the outer shell 152. The insulating material 170 is positioned on the side of the outer shell 152 that is configured to be positioned away from the patient 14. In some embodiments, the insulating material 170 is a reflective material.

Figure 7:
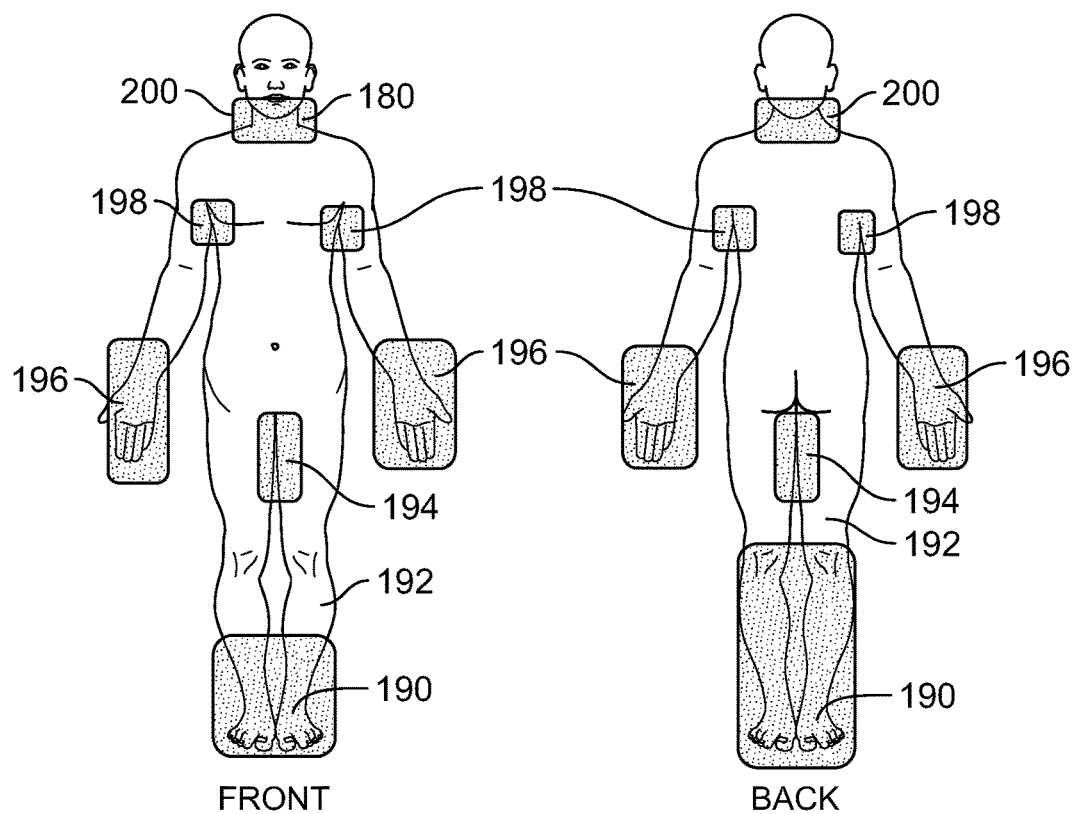
FIG. 7 is a top plan view of a patient covered with the warming device shown in FIG. 6.

Referring to FIG. 7, the device 150 is configured as pads or patches 180 that are positioned on parts of the patient's body where the patient's blood flow is proximate to the patient's skin and a thickness of the patient's fat is limited. In some embodiments, the warming device 150 has an adhesive layer to adhere the warming device 150 to the patient's skin. The areas of the patient's skin that are covered by the pads 180 are selected based on areas that may require additional heating. Optionally, the pads 180 may include a charging device that maintains the melting point of the phase change material 160. The pads 180 may be electrically coupled by cables 184 (shown in broken lines). In the illustrative embodiment, the areas of the patient 14 covered by the pads 180 includes the feet 190, the lower legs 192, the inner thighs 194, the hands 196, the armpits 198, and the neck 200. It should be noted that the pads 182 may be positioned on any part of the patient's body. Additionally, in some embodiments, the device 150 may be configured as a blanket.

Figure 8:
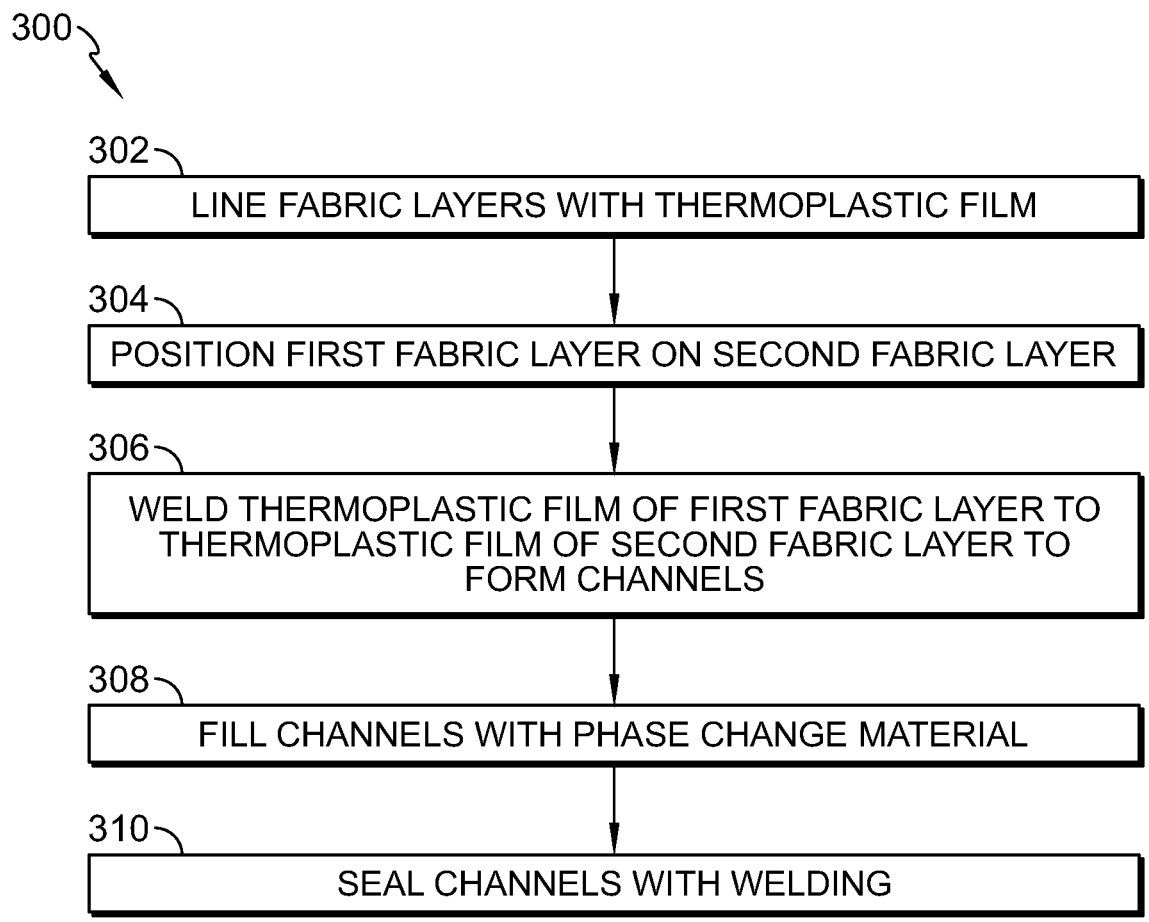
FIG. 8 is a routine for manufacturing the device shown in FIGS. 1-4.

Referring to FIG. 8, a routine 300 is provided for manufacturing the warming device 16. It should be note that at least some of the steps of the routine 300 may be used to manufacture the warming device 150. At block 302, the fabric layers 30, 32 are coated with a thermoplastic film 34. The fabric layer 30 is then positioned on the fabrics layer 32 so that the thermoplastic film 34 of the fabric layer 30 is positioned adjacent the thermoplastic film 34 of the fabric layer 32, at block 304. The two thermoplastic films 34 are then welded together using radio-frequency welding, ultrasonic welding, or bonding, at block 306, to form at least one channel 64. The channel 64 is formed with an open end. In the embodiments described above, a plurality of channels 64 is formed. A first plurality of the channels 64 has an open end 66 on a first side of the warming device 16, and a second plurality of channels 64 has an open end 66 on a second side of the warming device 16.

At block 308, each channel 64 is filled with phase change material 42. For example, the channels 64 are filled through the respective open end 66. That is the open end 66 may be positioned upward so that the phase change material 42 is gravity feed into the channels 64. Once the channels 64 are filled with phase change material 42, the open ends 66 of the channels 64 are welded closed. In some embodiments, the first plurality of channels 64 is filled with phase change material 42 and the respective open ends 66 are welded closed. The warming device 16 is then inverted so that the open ends 66 of the second plurality of channels 64 faces upward. The second plurality of channels 64 are then filled with the phase change material 42 and the respective open ends 66 of the second plurality of channels 64 are welded closed at block 310.

Figure 9:
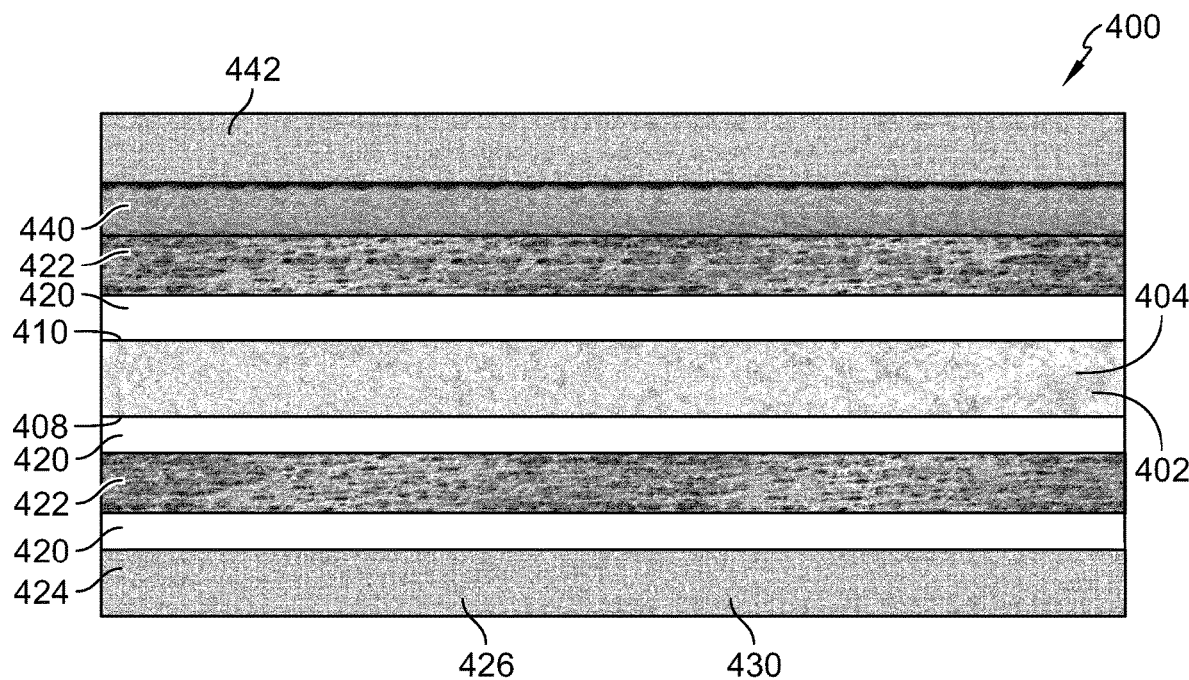
FIG. 9 is a cross-sectional view of another embodiment of a warming blanket.

Referring to FIG. 9, a warming device 400 includes a batting layer 402 including batting 404 infiltrated with microencapsulated phase change materials (PCMs) 406. The batting layer 402 has a patient side 408 configured to face a patient using the warming device 400. The batting layer 402 also includes an upper side 410 that faces away from the patient when the patient is using the warming device 400. A sealant 420 is applied to the patient side 408 and the upper side 410 to seal the PCMs 406 within the batting 404. A hot melt fabric adhesive 422 applied to both the patient side 408 and upper side 410 of the batting layer 402 outside of the sealant 420. A first fabric layer 424 is adhered to the hot melt fabric adhesive 422 on the patient side 408 of the batting layer 402. The first fabric layer 424 includes a PCM integrated coating 426. Another sealant 420 is applied to the first fabric layer 424 between the first fabric layer 424 and the hot melt fabric adhesive 422. An insulation layer 440 is adhered to the hot melt fabric adhesive 422 on the upper side 410 of the batting layer 402. A second fabric layer 442 is coupled to the insulation layer 440 and faces away from the patient.

The PCM integrated coating 426 permeates the first fabric layer 424 and the surface of the first fabric layer 424 on one side of the first fabric layer 424. The coated side 426 of the first fabric layer 424 may face inward away from the patient. Alternatively, the coated side 426 of the first fabric layer 424 may face the patient and contact the patient's skin to optimize the sensation of warmth due to an increased rate of heat transfer. The coating 426 has high breathability as measured by moisture vapor transmission rate (MVTR) to allow perspiration to escape and to minimize increases in humidity. The coating 426 may incorporate flame retardants as needed to meet flammability standards. The first fabric layer 424 is a loose weave with drape and hand comparable to knit cotton blankets used in hospitals. Alternatively, the first fabric layer 424 could be a conventional thermal blanket. Loose weave fabrics hold more coating than a tight weave, due to more space between fibers.

The first fabric layer 424 is preferably a cotton-polyester blend to improve durability of PCM coating which is water-soluble because the cotton is hydrophilic. The polyester improves durability of fabric. The first fabric layer 424 is approximately 70 inches wide and approximately 90 inches long, or the size of conventional thermal blankets. A larger size would allow wrapping of the blanket underneath body. Alternatively, to reduce costs, the PCM-coating width may be less than the blanket width. Rather than applying a coating 426 that only partially covers the fabric width, three sections may be stitched together. A middle section may be completely coated from edge to edge with a conventional coating method. Side sections may be uncoated and stitched together to middle section with stitching methods that hide the seam.

Microencapsulated PCMs 430 are mixed into the fabric coating 426. The microencapsulated PCMs have a polymer shell coating around a phase change material that maintains a solid appearance even through phase changes. A non-encapsulated PCM changes between solid and liquid states. Most microencapsulated PCMs are paraffins similar to candle wax. Microencapsulated PCMs 430 appear as a fine powder due to a very small particle size of approximately 20 microns. The microencapsulated PCMs 430 may be provided as a wet cake or liquid dispersion form that can be easily mixed into a water-based coating compound. Wet cake has smaller particles than dry powder, and is less expensive. The microencapsulated PCMs 430 are non-toxic and much less flammable than a non-encapsulated PCM. Thus, the need for flame retardants may be avoided.

The microencapsulated PCMs 430 have a phase change temperature between 38 degrees Celsius and 44 degrees Celsius. The PCMs 430 will hold the temperature around the phase change temperature as it cools from above to below that temperature. This is because energy is released as molecular bonds are broken as the PCM transitions from liquid to solid phase. The surface temperature of the warming blanket 400 in contact with the skin should not exceed 41 degrees Celsius, which is an IEC standard, but the contact surface temperature of the warming blanket 400 is lower than the PCM temperature due to layers such as fabrics and insulation liners limiting heat transfer. The blanket's contact surface temperature must be higher than average skin temperature to induce a sensation of warmth. A human body's average skin temperature is around 33 degrees Celsius, but rises toward the core temperature of 37 degrees Celsius when the body is well-insulated. It takes 60-90 minutes to reach this level without active warming, but the application of heat can accelerate this temperature increase, and even cause the skin temperature to rise above 37 degrees Celsius with a higher contact surface temperature.

A combination of PCM melting temperatures may be employed to smooth out the temperature gradient and improve patient comfort. The phase change temperature being lower than the blanket warming temperature of 54 degrees Celsius allows the warming blanket 400 to quickly cool to that temperature and thus reach the safe contact surface temperature of 41 degrees Celsius. Multiple phase change temperature options may be provided to meet varying user preferences such as warm (37 degrees Celsius), very warm (39 degrees Celsius), and hot (41 degrees Celsius). Alternative embodiments may include PCM temperatures lower than 38 degrees Celsius and higher than 44 degrees Celsius. It is possible to keep a patient comfortable with a higher PCM temperature than the ambient room temperature which is generally between 20 degrees Celsius and 25 degrees Celsius. Thus, a PCM temperature as low as 25 degrees Celsius may deliver comfort. It is possible to use a PCM temperature higher than 44 degrees Celsius and still deliver a contact surface temperature at or below the desired temperature of 41 degrees Celsius. This is made possible using low-thermal conductivity materials such as insulation and fabrics which have high insulation. The PCMs 430 should have a high latent heat, preferably over 200 KJ/kg. A high latent heat allows the blanket to feel warm over a longer duration. A high latent heat allows as smaller amount of PCM 430 to be used, which minimizes the thickness, weight, and cost of the warming blanket 400.

The fabric coating 426 is flexible to improve drape and hand of the fabric to improve customer acceptance. The fabric coating 426 is durable to retain PCM particles from being washed out in laundry cycles. Heat-retaining performance would be compromised if PCM particles 430 were washed out. A more durable coating 426 allows the warming blanket 400 to be used more often, and thus reduces its cost per use. The warming blanket 400 may be colored or otherwise marked to make it easily distinguished from conventional warming blankets. The warming blanket 400 may also have labels that minimize the likelihood it will be removed from the perioperative unit.

The batting layer 402 includes an inner liner of loosely-packed quilt batting that hold a larger mass of PCM coating than a thinner fabric that comes into direct contact with skin. The additional PCM facilitates improving the drape and hand of the warming blanket 400 by reducing the PCM mass that is coated onto the fabric in contact with the skin. The loosely-packed batting holds more coating/PCM than a tightly-woven fabric.

The insulation layer 440 above the phase change material facilitates minimizing heat loss to the ambient room environment, and thus allows the PCM to retain a higher temperature over a longer duration. The insulation layer 440 also reduces the mass of PCM needed which impacts weight, thickness, cost, and improves patient comfort. There is no insulation liner between the PCM and the human body because this would have the effect of lowering the contact surface temperature and thus compromising the feeling of warmth. In some embodiments, the insulation layer 440 may include Thinsulate® or Primaloft®. In some embodiments, the insulation layer 440 may be cotton, polyester, or cotton/poly thermal batting/interfacing. A thermal conductivity of the insulation layer may be approximately 0.04 W/m·K or less.

The hot melt fabric adhesive 422 is used to hold the PCM-coated quilt batting layer 402, insulation liner 440, and possibly other layers in place. The inner liners need to be fastened in place to prevent redistribution and bunching up, especially in laundry cycles. The hot melt fabric adhesive 422 is flexible to avoid negatively impacting drape and hand of fabric. The hot melt fabric adhesive 422 may be a powder or hot melt adhesives converted into a nonwoven fabric. Fire retardants may be mixed into the hot melt fabric adhesive 422 to optimize compliance to flammability codes and standards.

The sealant 420 facilitates increasing durability of the PCM-integrated coating 426. Additionally, a sealant 420 may be used to improve the durability of fabric coatings developed to retain PCM microcapsules 430 which typically have compromised durability due to the need to retain the fabric's drape and hand. The sealant 420 is applied directly to the coating 426 and, in some embodiments, mixed into the coating 426. In some embodiments, the hot melt fabric adhesive 422 may deliver the protection that would otherwise be provided by a sealant 420. Thus, in such embodiments, the sealant 420 may not be necessary where a fabric adhesive is able to provide this protection. The sealant 420 is highly breathable, with high MTVR, to facilitate minimizing humidity below the blanket.

Figure 10:
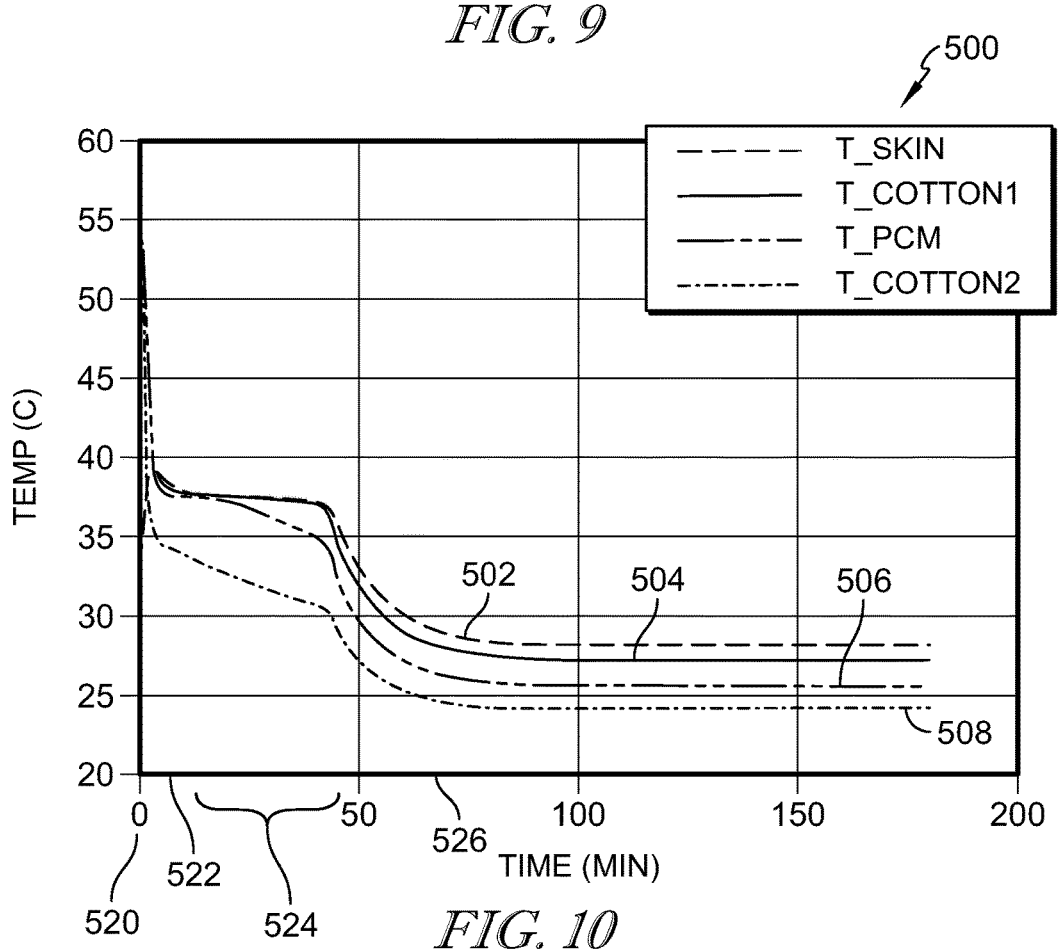
FIG. 10 is a graph illustrating heat retention in the warming blanket shown in FIG. 9.

Referring to FIG. 10, a graph 500 illustrates the heat retention of the warming blanket 400. Specifically, the graph 500 illustrates the heat retention of the patient's skin in line 502, the heat retention of the first fabric layer 424 in line 504, the heat retention of the PCMs 430 in line 506, and the heat retention of the second fabric layer 442 in line 508.

Referring to line 502, the patient's skin is approximately 33 degrees Celsius before the warming blanket 400 is applied at time 520. After applying the warming blanket 400 to the patient's skin, the temperature of the patient's skin increases to 39 degrees Celsius at time 522, which is approximately 2 minutes. The temperature of the patient's skin then drops to approximately 38 degrees Celsius for a time period 524 of approximately 45 minutes. After the time period 524, the temperature of the patient's skin begins to exponentially decrease to a temperature of approximately 28 degrees Celsius at time 526.

Referring to line 504, the first fabric layer 424 has a temperature of approximately 54 degrees Celsius at time 520 when the warming blanket is removed from the warming cabinet. After applying the warming blanket 400 to the patient, the temperature of the first fabric layer 424 decreases to approximately 38 degrees Celsius at time 522. This temperature is retained throughout the time period 524. After the time period 524, the temperature of the first fabric layer 424 exponentially decreases to a temperature of approximately 27 degrees Celsius at time 526.

Referring to line 506, the PCMs 430 have a temperature of approximately 54 degrees Celsius at time 520 when the warming blanket is removed from the warming cabinet. After applying the warming blanket 400 to the patient, the temperature of the PCMs 430 decreases to approximately 38 degrees Celsius at time 522. This temperature gradually decreases throughout the time period 524 to a temperature of approximately 35 degrees Celsius. After the time period 524, the temperature of the PCMs 430 exponentially decreases to a temperature of approximately 26 degrees Celsius at time 526.

Referring to line 508, the second fabric layer 442 has a temperature of approximately 54 degrees Celsius at time 520 when the warming blanket is removed from the warming cabinet. After applying the warming blanket 400 to the patient, the temperature of the second fabric layer 442 decreases to approximately 34 degrees Celsius at time 522. This temperature gradually decreases throughout the time period 524 to a temperature of approximately 30 degrees Celsius. After the time period 524, the temperature of the second fabric layer 442 exponentially decreases to a temperature of approximately 24 degrees Celsius at time 526.

Accordingly, the warming blanket 400 can maintain a temperature of the patient's skin for approximately 45 minutes before the warming blanket 400 needs to be replaced. This maintenance of temperature reduces the number of times that a caregiver has to change the patient's warming blanket 400 in comparison to other warming blankets. The warming blanket 400 maintains heat longer than conventional cotton warming blankets which lose heat in one or two minutes. Caregivers and other staff can use the warming blanket 400 without making changes to their work processes, thus enhancing the likelihood of customer adoption. The warming blanket is configured to be pre-heated in the warming cabinet along with traditional cotton warming blankets. The warming blanket 400 maintains a cotton feel and the temperature stays within a comfortable range without overheating or burning the patient. The warming blanket 400 is reusable and only one blanket is needed at a time, thereby reducing trips to the warming oven to replace cooled blankets. Additionally, a heavier weight of the warming blanket 400 provides comfort to the patient.

Although this disclosure refers to specific embodiments, it will be understood by those skilled in the art that various changes in form and detail may be made without departing from the subject matter set forth in the accompanying claims.

The invention claimed is:

1. A warming device, comprising:
   a batting layer having a phase change material, the batting layer having a patient side and an upper side,
   a hot melt fabric adhesive applied to the patient side and upper side of the batting layer,
   a first fabric layer adhered to the hot melt fabric adhesive on the patient side of the batting layer, the first fabric layer having a phase change material integrated coating,
   an insulation layer adhered to the hot melt fabric adhesive on the upper side of the batting layer, and
   a second fabric layer coupled to the insulation layer.

2. The warming device of claim 1, wherein the batting layer includes loosely-packed quilt batting.

3. The warming device of claim 1, wherein the first fabric layer includes microencapsulated phase change materials mixed into a fabric coating.

4. The warming device of claim 3, wherein the microencapsulated phase change materials include a polymer shell coating around that maintains a solid appearance through phase changes between solid and liquid states.

5. The warming device of claim 3, wherein the microencapsulated phase change materials have a melting point temperature between 38 degrees Celsius and 44 degrees Celsius.

6. The warming device of claim 3, wherein the microencapsulated phase change materials have a latent heat of over 200 KJ/kg.

7. The warming device of claim 1, further comprising a sealant between the patient side of the batting layer and the hot melt fabric adhesive, and a sealant between the upper side of the batting layer and the hot melt fabric adhesive.

8. The warming device of claim 7, further comprising a sealant between the first fabric layer and the hot melt fabric adhesive on the patient side of the batting layer.

9. The warming device of claim 1, wherein the hot melt fabric adhesive is non-woven.

10. The warming device of claim 1, wherein the hot melt fabric adhesive is formed from a powder.

11. The warming device of claim 1, wherein the first fabric layer is formed from cotton.

12. The warming device of claim 1, wherein the first fabric layer is formed form a poly fabric.

13. The warming device of claim 1, wherein the second fabric layer is formed from cotton.

14. The warming device of claim 1, wherein the second fabric layer is formed from a poly fabric.

15. The warming device of claim 1, wherein the insulation layer is formed from polyester fiber.

* * * * *